(12) United States Patent
Chan et al.

(10) Patent No.: US 7,585,664 B2
(45) Date of Patent: Sep. 8, 2009

(54) INTEGRATED CIRCUIT OPTICAL DETECTOR FOR BIOLOGICAL DETECTION

(75) Inventors: Mansun Chan, Kowloon (CN); Jiong Li, Kowloon (CN); Yijin Wang, Kowloon (CN); Zuhong Lu, Nanjing (CN)

(73) Assignee: The Hong Kong University of Science and Technology, Hong Kong (HK)

( * ) Notice: Subject to any disclaimer, the term of this patent is extended or adjusted under 35 U.S.C. 154(b) by 624 days.

(21) Appl. No.: 10/965,270

(22) Filed: Oct. 14, 2004

(65) Prior Publication Data

US 2006/0084069 A1    Apr. 20, 2006

(51) Int. Cl.
| | |
|---|---|
| *C12M 1/00* | (2006.01) |
| *C12Q 1/70* | (2006.01) |
| *C12M 1/34* | (2006.01) |
| *C12M 3/00* | (2006.01) |
| *A01N 1/00* | (2006.01) |
| *A01N 1/02* | (2006.01) |

(52) U.S. Cl. ................. 435/287.2; 435/6; 435/283.1; 435/309.4

(58) Field of Classification Search .............. 435/6, 435/283.1–309.4
See application file for complete search history.

(56) References Cited

U.S. PATENT DOCUMENTS 5,073,483 A    12/1991  Lebacq
5,075,793 A *  12/1991  Schiffner .................. 398/203

(Continued)

OTHER PUBLICATIONS

Csáki et al., "The optical detection of individual DNA-conjugated gold nanoparticle labels after metal enhancement", Institute of Physics Publishing, Nanotechnology 14, 2003, pp. 1262-1268.

(Continued)

*Primary Examiner*—Walter D Griffin
*Assistant Examiner*—Lydia Edwards
(74) *Attorney, Agent, or Firm*—Conley Rose, P.C.

(57) ABSTRACT

This invention provides an integrated circuit (IC) optical detector. The IC optical detector comprises a substrate and an IC. The substrate comprises a plurality of test sites defined thereon. The test sites comprise a surface suitably treated for coating of at least one test sample. The at least one test sample is capable of being changed by a reaction. The IC comprises at least one optical sensor array for simultaneously receiving and sensing optical signals from the test sites during operations Presence of at least one changed test sample at a test site changes the quantity of light directed through the test site. The change in quantity of light is detectable by the sensor array. The optical sensor array further converts the sensed optical signals to electrical signals. The IC automatically processes and outputs the electrical signals during operation.

This invention further provides a method for detecting a specific sample within at least one test sample. The method comprises securing said test sample on a plurality of test sites defined on a substrate; processing said test sample to allow said test sample to be optically differentiated; directing a light at said test sample; simultaneously receiving and sensing optical signals from said test sample using at least one optical sensor array of an IC; converting said sensed optical signals to electrical signals by said optical sensor array; and automatically processing and outputting said electrical signals by said IC to detect said specific sample within said test sample.

14 Claims, 22 Drawing Sheets

U.S. PATENT DOCUMENTS

| | | | | |
|---|---|---|---|---|
| 5,538,850 | A * | 7/1996 | King et al. | 435/6 |
| 6,168,748 | B1 * | 1/2001 | Wang et al. | 264/520 |
| 6,197,503 | B1 * | 3/2001 | Vo-Dinh et al. | 435/6 |
| 6,251,685 | B1 * | 6/2001 | Dorsel et al. | 436/172 |
| 6,890,741 | B2 * | 5/2005 | Fan et al. | 435/91.2 |
| 6,946,286 | B2 * | 9/2005 | Howard | 435/287.2 |
| 7,378,280 | B2 * | 5/2008 | Quake et al. | 436/63 |
| 2002/0006632 | A1 * | 1/2002 | Ponnampalam et al. | 435/7.92 |
| 2002/0018199 | A1 * | 2/2002 | Blumenfeld et al. | 356/73 |
| 2002/0022261 | A1 * | 2/2002 | Anderson et al. | 435/287.2 |
| 2002/0146714 | A1 * | 10/2002 | Lieber et al. | 435/6 |
| 2002/0162947 | A1 * | 11/2002 | Weitekamp et al. | 250/214 R |
| 2002/0172969 | A1 * | 11/2002 | Burns et al. | 435/6 |
| 2003/0003457 | A1 * | 1/2003 | Golovlev | 435/6 |
| 2006/0147927 | A1 * | 7/2006 | Geddes et al. | 435/6 |

OTHER PUBLICATIONS

Global Spec., online at: http://video-equipment.globalspec.com/LearnMore/Sensors_Transducers_Detectors/Vision . . . , "GlobalSpec.com, Imaging and video Equipment, Image Sensors, CMOS Image Sensors, Learn more", 1999-2004, 3 pgs.

Flandre et al., "On-chip DNA electrical detection based on Si-CMOS compatible AI capacitors and inductors coated with metal oxides", Microelectronics Lab, DNA workshop Liège, UCL, Sep. 2, 2004, 18 pgs.

Fritzsche et al., online at: http://www.ipht-jena.de/BEREICH_3/english/molnano/mngold_en.html, "Gold nanoparticles—novel marker for DNA chips," Biotechnical Microsystems Dept./Molecular Nanotechnology Group, 3 pgs.

Kricka, Larry J., online at: http://clinchem.org/cgi/content/full/45/4/453, "Nucleic Acid Detection Technologies—Labels, Strategies, and Formats", Clinical Chemistry 45: 453-458, 1999, 10 pgs.

Thornton et al., online at: http://photoscience.la.asu.edu/bionano/research6.htm, "Hybrid Biomolecular-CMOS Integrated Circuits", 3 pgs.

"Fully Electronic DNA Sensor Arrays on CMOS" Research Trends, A publication by Corporate Research, Oct. 2002, 2 pgs.

"What Is The Difference Between CCD And CMOS Image Sensors In A Digital Camera?," online at: http://electronics.howstuffworks.com/question362.htm, 2 pgs.

* cited by examiner (b) 30mins (a) 5mins

INTEGRATED CIRCUIT OPTICAL DETECTOR FOR BIOLOGICAL DETECTION

FIELD OF INVENTION

The present invention is related to an optical detector, and particularly to an integrated circuit (IC) optical detector used for biological sample detection.

BACKGROUND OF INVENTION

The introduction of high-density DNA micro-arrays has significantly reduced the time and cost for DNA detection through miniaturization and automation that are made available by some advanced IC fabrication technologies. The dominant DNA micro-array based detection systems rely on fluorescence or radioactive methods to discriminate matched (ie hybridized) and unmatched (unhybridized) DNA samples for a given testing probe. Referring to FIG. 1, conventionally, a solid support (eg a DNA array chip) 10 with DNA probes 12 is provided as shown in FIG. 1(a). It is to be noted that this DNA "chip" is not related to a packaged integrated circuit device which is also called a "chip". The sample DNA fragments 14 typically have one or more fluorescent labels. The sample DNA fragments 14 are applied to the DNA array chip 10. If any of the sample DNA fragments 14 match the DNA probes 12, the DNA fragments 14 with the fluorescence label are captured or bound by the DNA probes 12, which is called hybridization as shown in FIG. 1(). If the DNA fragments 14 do not match the probes 12, the DNA fragments 14 are washed away by the subsequent cleaning steps and no fluorescence will be associated with those unmatched DNA probes on the DNA array chip 10. To detect the matching of DNA sample 14 with the probes 12, an expensive UV light source 16 is usually required to excite the fluorescence label as shown in FIG. 1(c). In addition, the detection is either based on microscope, or photographic system that can detect color. Thus, the process is relatively expensive and inconvenient. Further, such conventional method requires specific color filters that are composed of very complicated film structure. Finally, the fluorescence and radioactive signal intensity degrade with time and can cause large variations in the sampled data, such that the testing result might be unreliable.

Instead of fluorescent labels, nano-metallic particles can be used as labels. Compared with the fluorescence based detection method, a nano-particle based DNA detection method has the advantages of: (1) physical properties (such as conductivity and opacity) that are easier to be electronically detected; (2) signal is stable with time; (3) fewer external components needed. These 3 advantages lead to more consistent experimental results. Some previous work using the conducting property of the metal particles has been proposed but it requires modifications to the CMOS process to include inert metal (such as gold or platinum) and different surface passivation techniques. Also it is difficult to process the conduction data using noise reduction techniques.

It is therefore the object of the present invention to provide an improved detection method and detector for test samples, particularly biological samples such as proteins and nucleic acids.

SUMMARY OF INVENTION

In accordance with the objects of the present invention, there is provided in one aspect an integrated circuit (IC) optical detector comprising a s and an IC. The substrate comprises a plurality of test sites defined thereon. The test sites comprise a surface suitably treated for coating of at least one test sample. The at least one test sample is capable of being changed by a reaction. The IC comprises at least one optical sensor array for simultaneously receiving and sensing optical signals from the test sites during operation. Presence of at least one changed test sample at a test site changes the quantity of light directed through the test site. The change in quantity of light is detectable by the sensor array. The optical sensor array further converts the sensed optical signals to electrical signals. The IC automatically processes and outputs the electrical signals during operation In another aspect of the present invention, there is provided a method for detecting a specific sample within at least one test sample. The method comprises securing said test sample on a plurality of test sites defined on a substrate; processing said test sample to allow said test sample to be optically differentiated, directing a light at said test sample; simultaneously receiving and sensing optical signals from said test sample using at least one optical sensor array of an IC; converting said sensed optical signals to electrical signals by said optical sensor array; and automatically processing and outputting said electrical signals by said IC to detect said specific sample within said test sample.

One of the major advantages of the present invention is that the IC optical detector and the method are fully CMOS compatible. Another advantage is that the detecting method is completely automated and so that the result is directly read out without external optical scanner needed Still another advantage is that the IC optical detector and the method provide a high sensitivity for low concentration detection compared with most existing systems. Still another advantage is that the IC optical detector and the method are capable of working with ordinary light sources instead of expensive and highly specific UV light sources.

DETAILED DESCRIPTION

Overview Of The Invention

The present invention provides an integrated circuit (IC) optical detector which incorporates a test sample capturing surface directly over the IC sensor array. The description that follows will first teach how the optical detector may be fabricated followed by how test samples may be captured or bound to the surface. The description will then teach how the test samples are detected or even quantified by the optical detector of the present invention. The description further teaches a few experimental results of the optical detector.

Structure of the IC Detector

Figure 1:
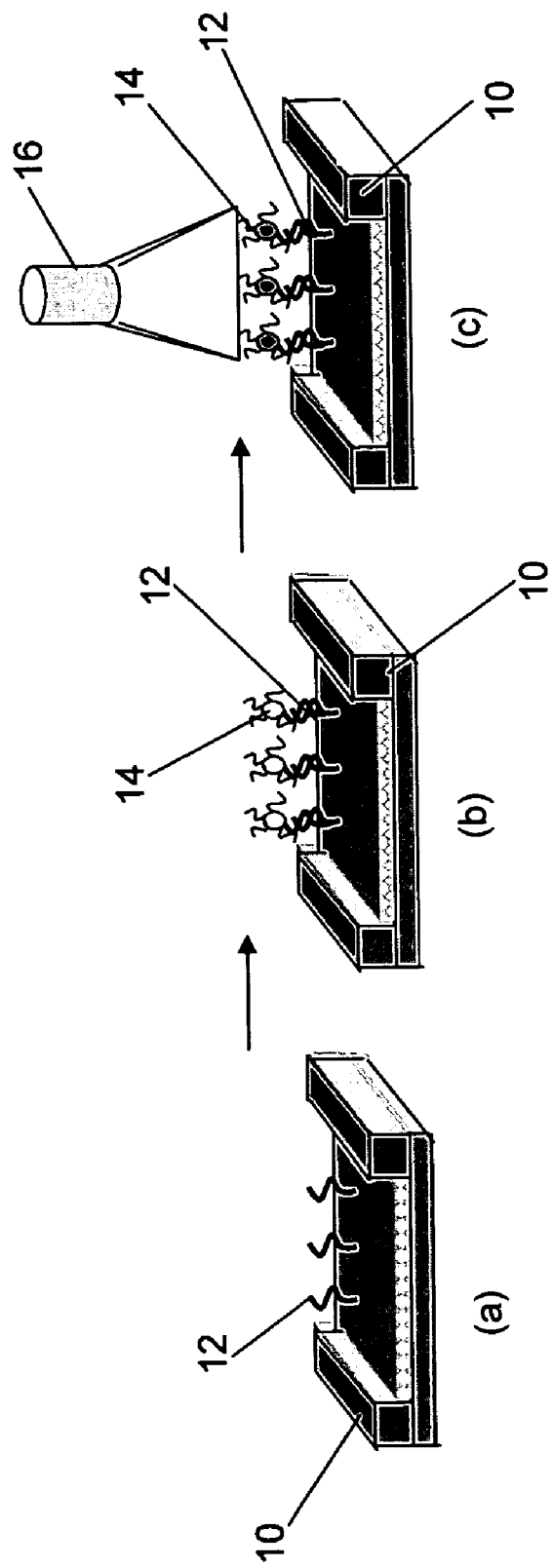
FIG. 1 is a schematic diagram showing the process of conventional DNA detection with fluorescence labeling technique.
Figure 2:
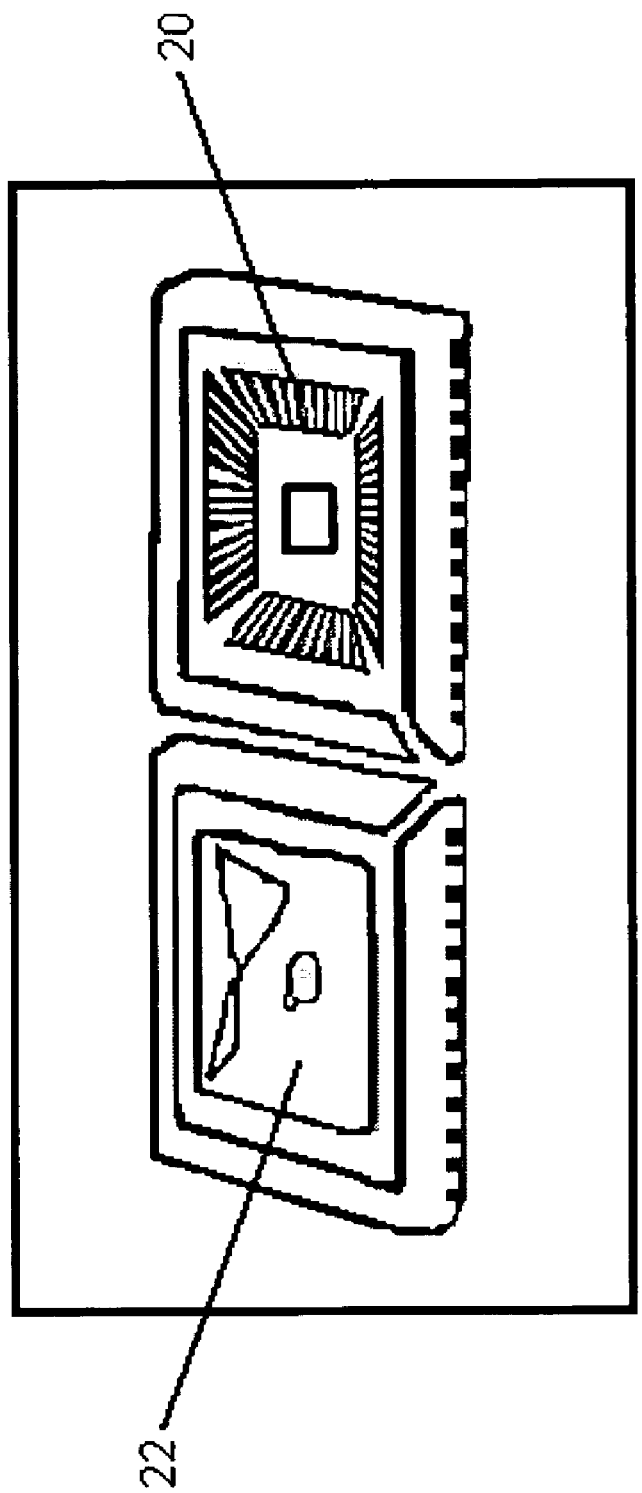
FIG. 2 is a perspective view of a packaged IC optical detector according to a preferred embodiment of the present invention.

Now referring to FIG. 2, a packaged integrated circuit (IC) optical detector 20 is provided In addition, gel can be used to cover the metal bonding wire for protection from chemical solutions as shown by the IC optical detector 22. In particular, the detector 20 can be fabricated with standard CMOS process as the passivation oxide/nitride can directly used as solid support. Since the active pixel sensor (APS) array has a very high density, it allows a number of sensor cells to be covered to provide redundancy and noise reduction Further, a number of sensitivity enhancement techniques described later can be used to detect DNA with extremely low concentration. In one embodiment, the detector 20 is fabricated using a HP 0.5 µm process that is well-known in the art. The packaging is done in a conventional manner with the metal wire bonding covered by a gel layer for protection. Only the sensor array is exposed.

Figure 3:
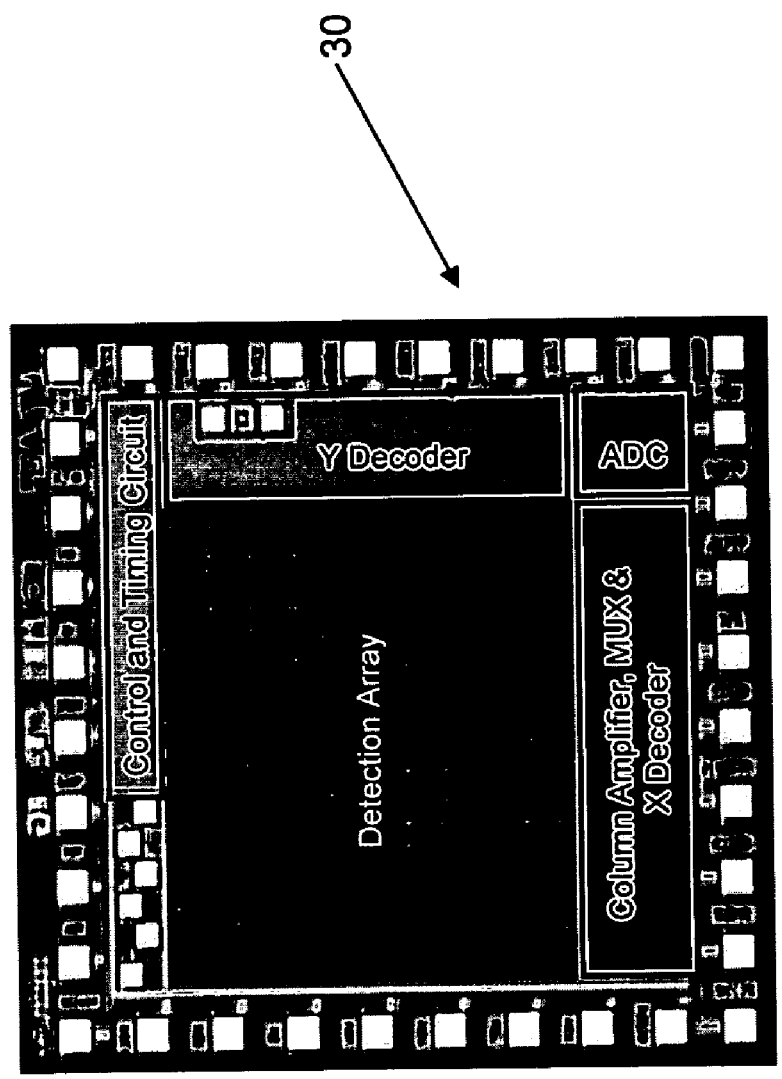
FIG. 3 is a die photo of the detector according to the preferred embodiment of the present invention.

In another embodiment, the IC optical detector 30 has 64×64 detection APS cells with the peripheral circuits fabricated using 0.5 mm CMOS process, whose die photo is shown in FIG. 3.

Figure 4:
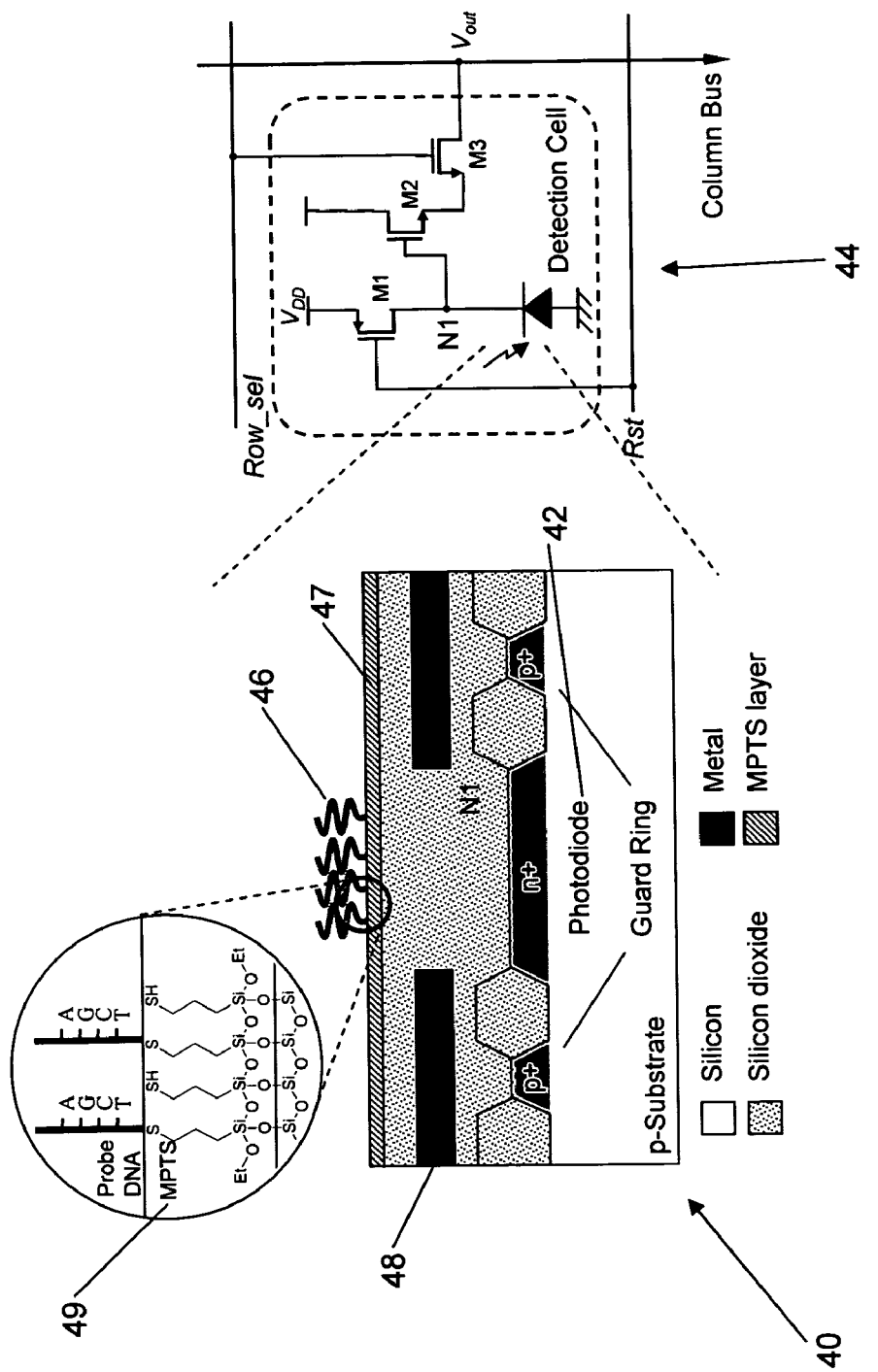
FIG. 4 is a cross-sectional view illustrating the APS structure of a detection cell of the detector according to the preferred embodiment of the present invention.

Now referring to FIG. 4, each detection cell 40 includes a photodiode 42 for sensing and APS 44 for readout. In one embodiment, the photodiode 42 is formed with an n+/p- structure, and the APS 44 is in traditional 3T structure. DNA probes 46 are attached on the surface 47 of the detection cell 40. A metal layer 48 is used to create an optical window and guard ring to prevent any crosstalk from the neighboring pixels. Each pixel can be randomly addressed with a 6-in-64-out X/Y decoder. The signals are readout sequentially from the pixel to the on-chip A/D converter (ADC) controlled by a 64-in-1-out analog multiplexer. In the ADC, there is a build-in correlated double sampling (CDS) circuit that reduces the process variations induced fixed pattern noise (FPN). In one embodiment, the cell size is 15×20 µm2 with a fill factor of 50%. Previously, the metal nano-particle color on a glass slides can be observed from microscope, but have not been put directly in contact with an IC chip. Based on the teaching of the present invention, the metal nano-particle can be deposited on the IC chip directly. As the nano-particle can effectively block the light source, no color filter is required to separate the background UV light from the excitation light and the signal fluorescence light. It allows the use of the chip as a direct solid support for the DNA hybridization. The fabricated DNA is fully compatible with the standard CMOS technology available in any common silicon foundries.

Bonding of DNA to Surface of Chip

After the chip fabrication, the chip surface 47 has to be modified in order to form covalent bonding with the DNA probes 46 as shown in FIG. 4. It is achieved by modifying a mercaptopropyltrimethoxysilane (MPTS) layer 49 to the top SiO2 passivation layer. The MPTS 49 serves as a bridge molecular layer to chemically connect DNA to silicon dioxide layer. The methoxyl groups on one end of the MPTS molecule can react with SiOH groups on the oxide surface. On the other end, the thiol group could react with another thiol group, which was chemically labeled on the 5 terminal of DNA probes 46. DNA probes 46 with known sequences are attached to the chip surface 47 by a pin spotter machine, Microprinting system (MicroSys™ 5100). In one embodiment, each spot size has a diameter of 100 µm and covering around 20 pixels to provide redundancy and reduce error reading. Some dummy rows/columns are left uncovered for background subtraction After the spotting, the chips were incubated in a humidified (wet) box overnight for the completion of immobilization reaction. Then the chips were cleaned with water and a black gel was glued on to the chip surface to cover bonding sites and the bonding metal lines, only exposing the area with the DNA probe. The insulation of the metal wire from the solution is important because the solution can potentially attack the metal lines and lead to malfunction of the system. After the protecting the bonding pads and metal wires, the chips were then ready to be used for DNA detection.

Detection of Signal

Figure 5:
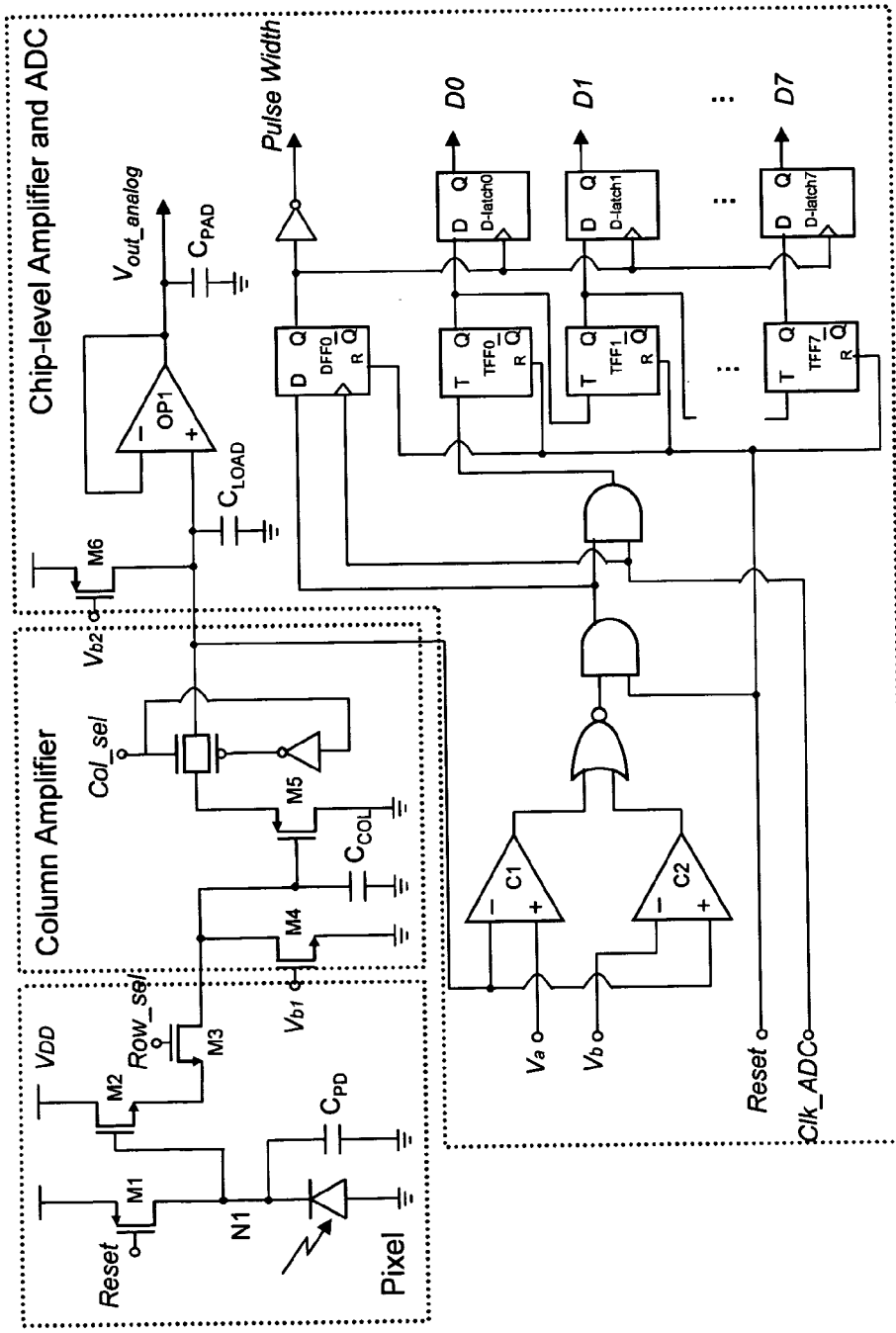
FIG. 5 is a diagram showing the architecture of the detector according to the preferred embodiment of the present invention
Figure 6:
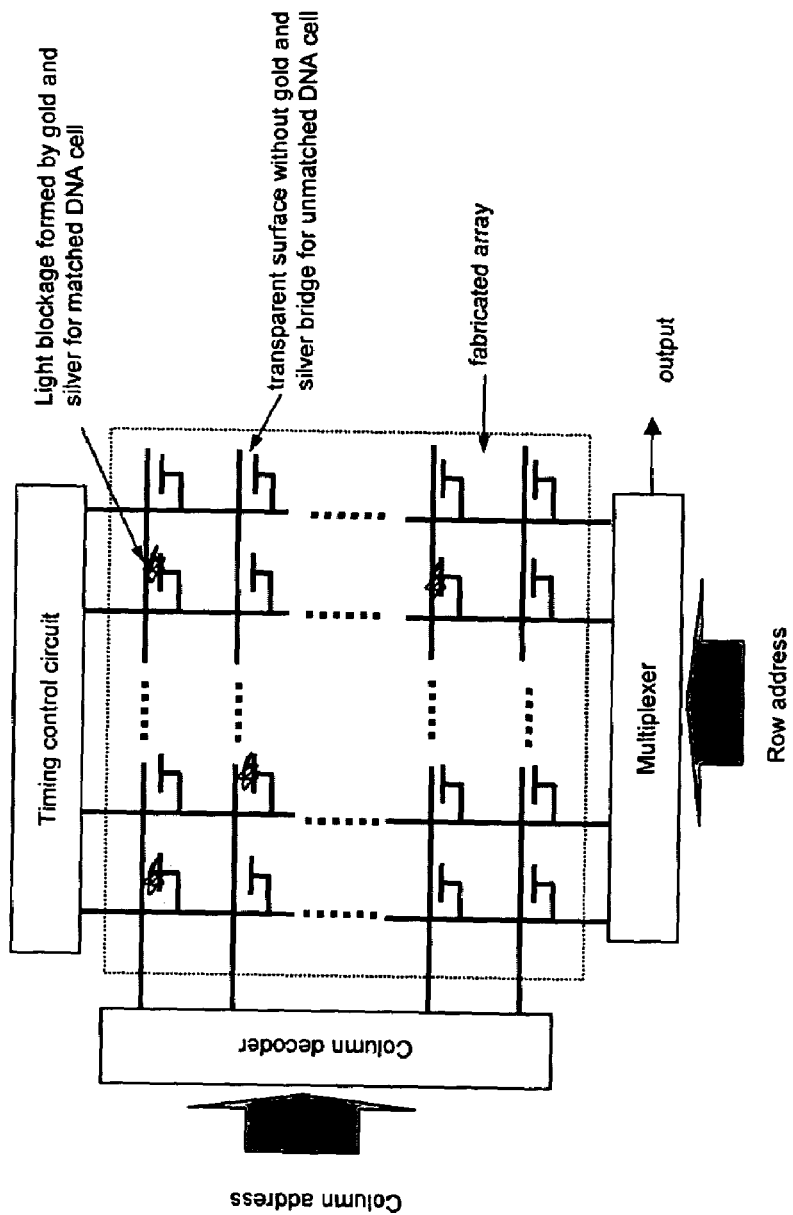
FIG. 6 is a schematic diagram showing the formation of photo-diodes with readout circuits of the detector according to the preferred embodiment of the present invention.
Figure 7:
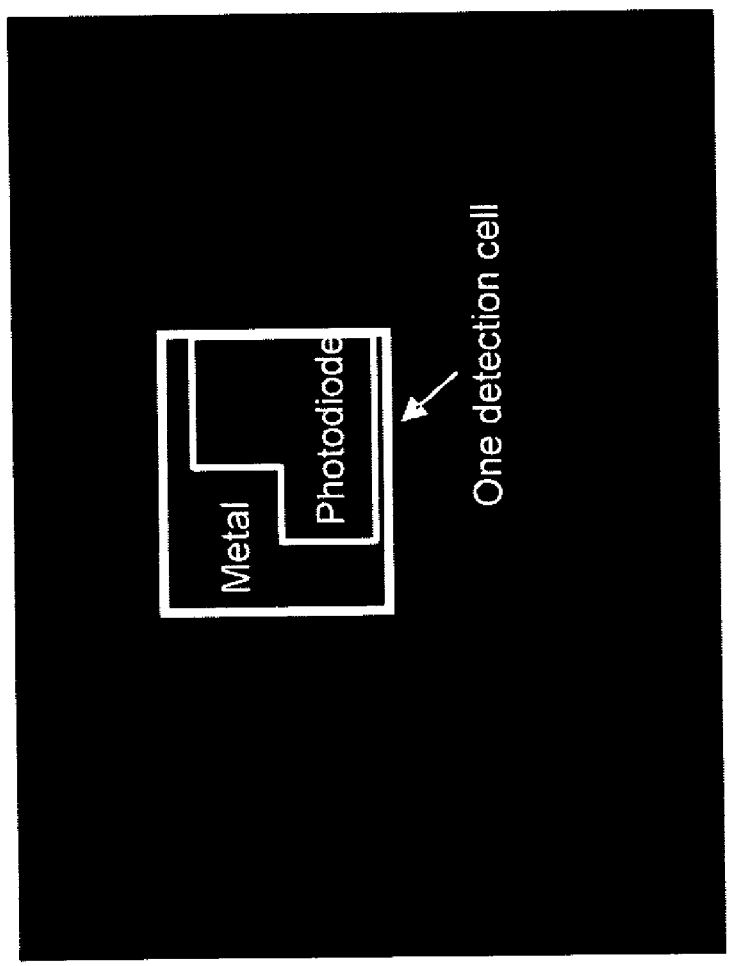
FIG. 7 is a micrograph of a small array of the detector according to the preferred embodiment of the present invention.

Now referring to FIG. 5, the circuit architecture including the APS, column amplifier, and chip level ADC is shown to indicate the data read our from the signal source. In one embodiment, the photodiode 42 can be put into an array structure for electrical readout as shown in FIG. 6. The sample can be applied to multiple cells in the array, and using averaging and differential amplification relative to a reference to reduce the fix pattern noise. FIG. 7 is a micrograph of a small array of DNA detection cell. The cell size is 20×15 μm2 with a fill factor of 50%. The circuit in the APS is covered by the metal, which serves as a light-shield.

Preferred Embodiment

Figure 8:
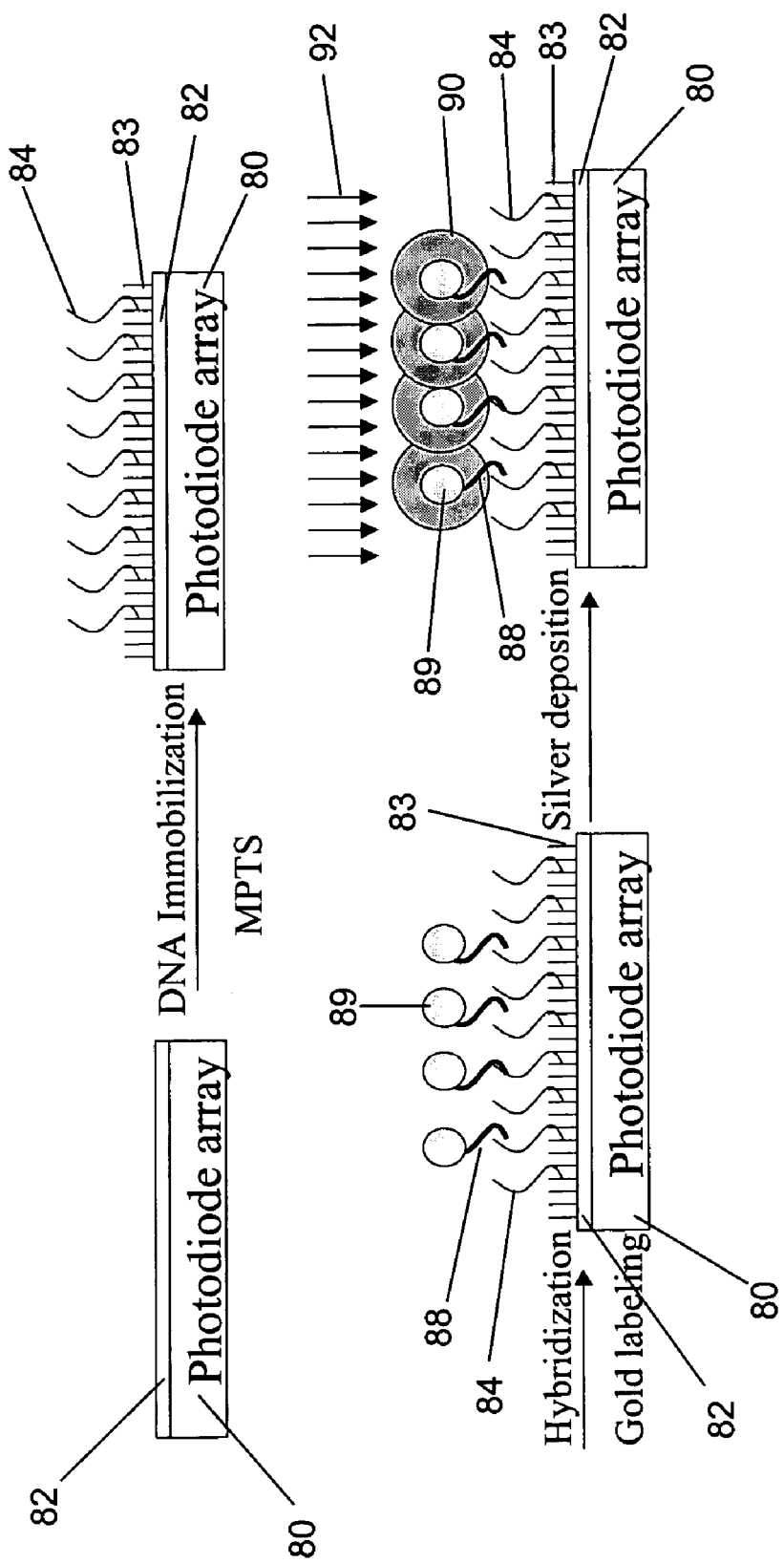
FIG. 8 is a schematic diagram showing a process for detecting a DNA sample according to one embodiment of the present invention.

FIG. 8 shows a preferred embodiment of the present invention, that of detection and identification of DNA sequences in a sample. The DNA fragment detection process using the IC optical detector is as described in previous Figures. Typically, the IC optical detector includes a substrate (not shown in FIG. 8) and an IC including at least one photodiode array 80. The photodiode array 80 can be CMOS image sensors or charge-coupled device (CCD) array. The surface 82 of the photodiode array 80 usually has a plurality of test sites and is modified in order to form covalent bonding with the a plurality of DNA probes 84 adapted for receiving at least one test sample. In one embodiment, the photodiode array 80 is formed within the substrate such that the surface 82 is the substrate surface.

Typically, a specific sample DNA 88 is modified with Adenosine polymer (poly A) tails. These sample DNA 88 may be applied to the photodiode array surface 82 in solution form by pipetting. If the sample DNA 88 has sequences complementary to that of any of the immobilized probes 84, it will be captured in a first hybridization step, while those mismatched DNA targets will be washed away in a subsequent washing step. In the second hybridization step, the IC chip is treated with a solution of oligonucleotide-modified gold nano-particles 89 with poly T tails that will attach to the poly A tails of the DNA targets 88 as the poly T sequences are complementary to the poly A tail sequences of the sample DNA. In this embodiment, the IC chip is washed, and then placed into a silver enhancer solution, which is composed of AgNO3 and hydroquinone, to deposit metal silver 90 around the gold particles 89. This step enhances the opaqueness at the location with gold particles 89 for signal enhancement. The surface 82 at locations with matched DNA will become more opaque leaving locations with mismatched DNA probes s transparent or less opaque.

Thereafter a light 92 is then directed to the photodiode array 80. In some situations, ambient light will suffice. The photodiode array 80 thus illuminated will simultaneously receive and sense the optical signals from the DNA targets 88 and the metal silver 90 around the gold particles 89. Because opaque particles 89 with matched DNA targets 88 block optical radiation, and the surface 82 at locations with mismatched DNA probes is still transparent or less opaque, the photodiode array 80 can sense the difference between the sites that have matched DNA and mismatched DNA. Further, the photodiode array 80 converts sensed optical signals to electrical signals and the IC 80 automatically processes and outputs electrical signals. Since only the DNA targets 88 that match one of the immobilized probes 84 are captured, the outputted electrical signals can indicate the DNA targets 88 that have been detected. Accordingly, such method to detect for DNA targets 88 using IC image sensor does not need color filter as the conventional methods do.

Figure 9:
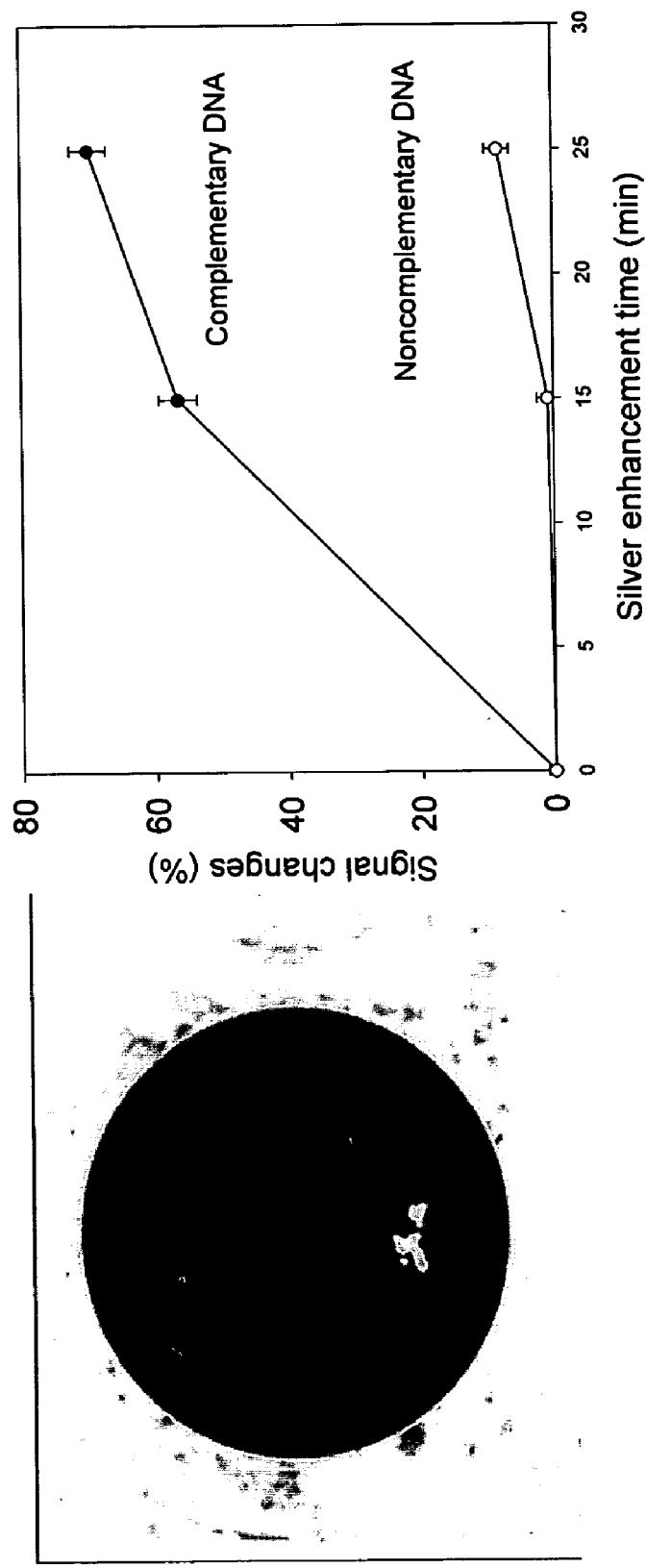
FIG. 9 shows experimental results of the observed surface of the detector after the process according to the present invention.

Referring to FIG. 9, the surface of hybridized DNA with process as described in FIG. 8 can be observed. In particular, the appearance at the photodiode location after hybridization of matched DNA together with the electrical characteristics measured is shown.

Typical Results

Figure 10:
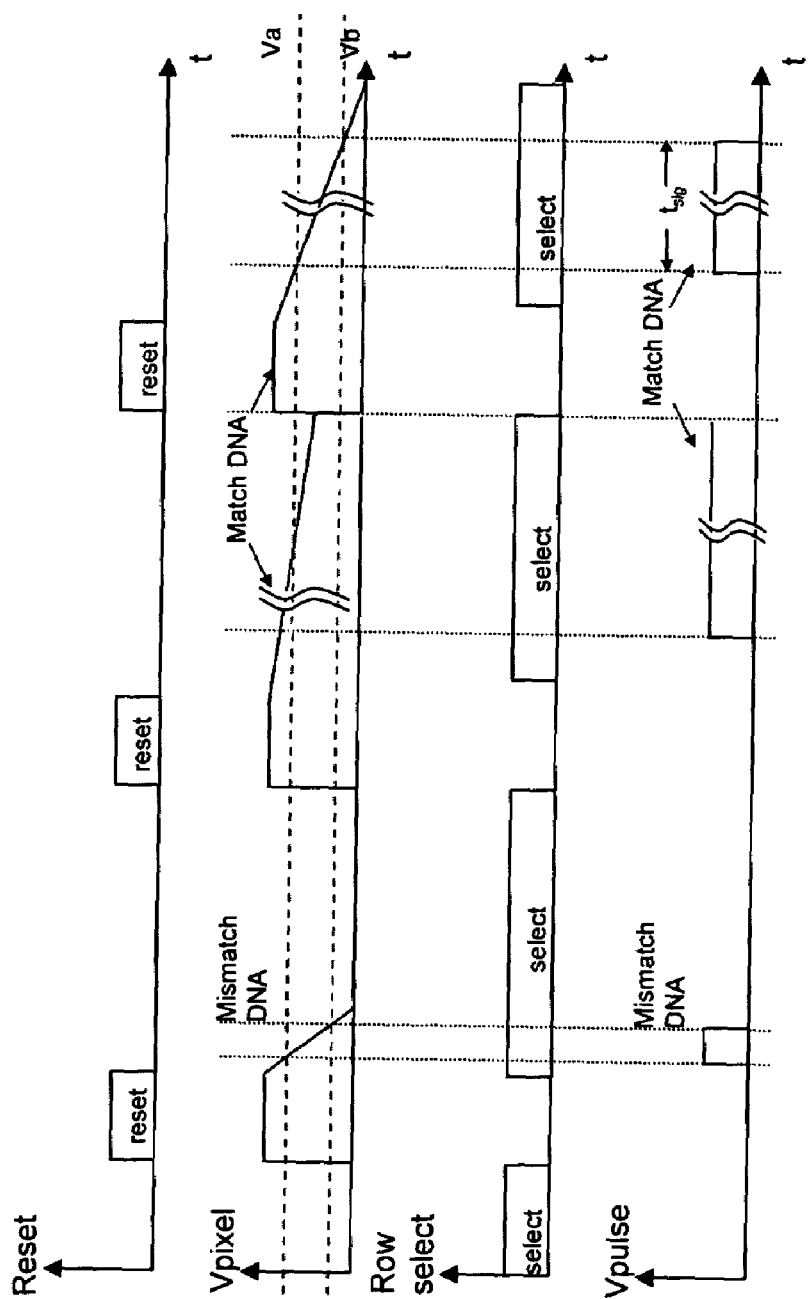
FIG. 10 is a diagram showing experimentally measured PWM scheme with adjustable parameters implemented for the readout circuit.

Referring to FIG. 10, the detection of hybridization of matched DNA is done by measuring the optical illumination intensity at the site with DNA probes. The optical signal is converted to an electronic signal by the photodiode, which is reflected by the rate of voltage drop (or the slope) at the output of each pixel. The slope is extracted by measuring the time required for the output voltage drop from one threshold Va to the other Vb. The output is a pulse width modulated voltage. The function is achieved by using a window comparator that generates the positive edge and the negative edge of a pulse when the pixel output signal crosses the two thresholds. The resulting pulse width is inversely proportional to the output slope and thus the signal strength of the photodiode. Finally, the pulse width is digitized with an on-chip 8-bit counter that outputs digital codes.

Features Of The Invention

Special attention should be dedicated in the design of electronic systems that interface with biological system. First of all, biological system is intrinsically much "noisier" than pure electronic system. In addition, the proposed system has to work with arbitrary light sources for consideration of portability. The variations in sample concentration can also affect the signal strength. The pulse-width modulation scheme used in the read-out circuit provides a mechanism to adjust the sensitivity of the system in both the voltage and time domain Two references voltages Va and Vb as well the clock frequency of the ADC (fADC) can be adjusted based on the feedback of array reading. In the case of strong light or extremely low concentration of mismatched DNA sample, the pulse width can become very small as the output voltage drops very fast. The system can adjust to this by increasing the A/D converter frequency (fADC). If under a condition of dim illumination or high sample concentration, a long pulse width will be generated and the sampling frequency has to be reduced to prevent overflow. In the case of the contrast between the cell with matched and mismatched DNA is too low, the system will adjust the references voltages Va and Vb to modify the sensitivity of the system.

Figure 11:
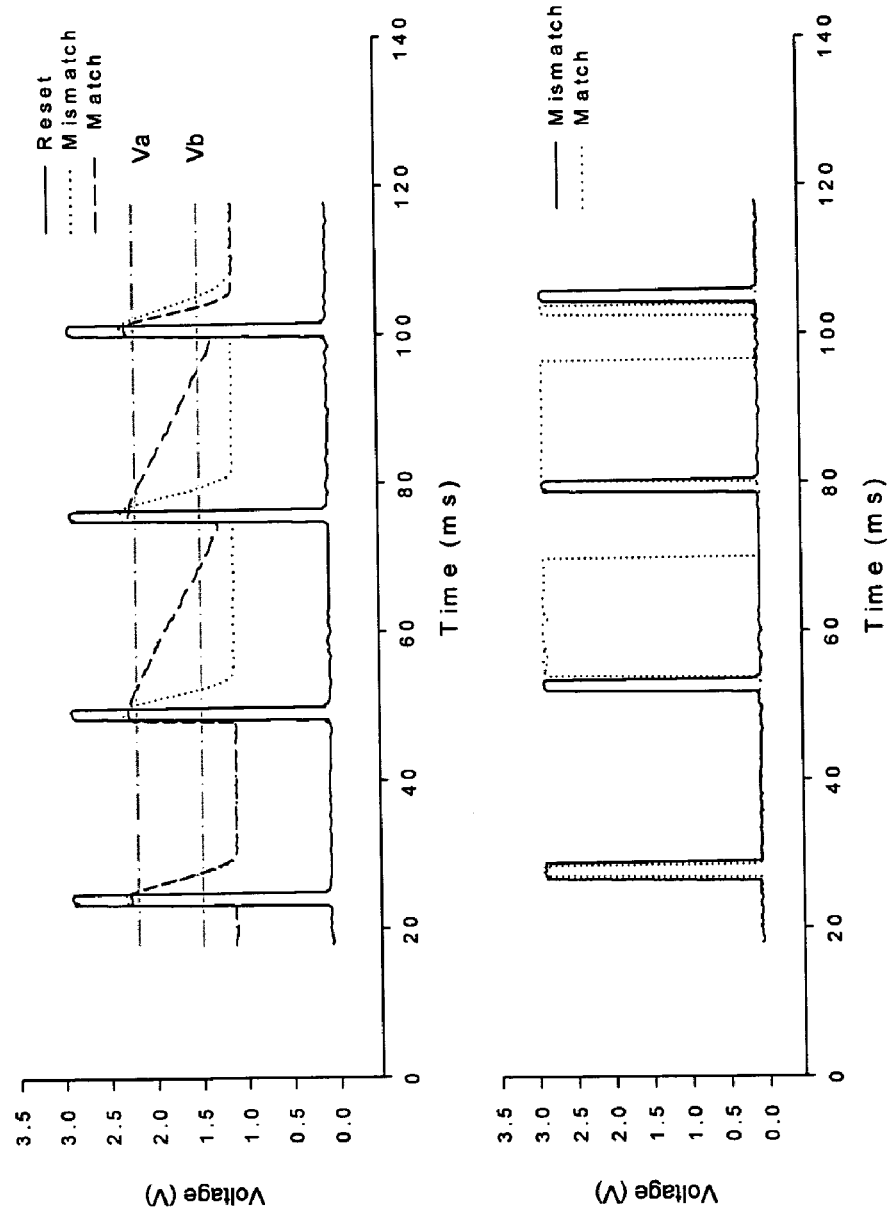
FIG. 11 is a diagram showing experimentally measured output waveform for cell location with matched and mismatched DNA sample.
Figure 12:
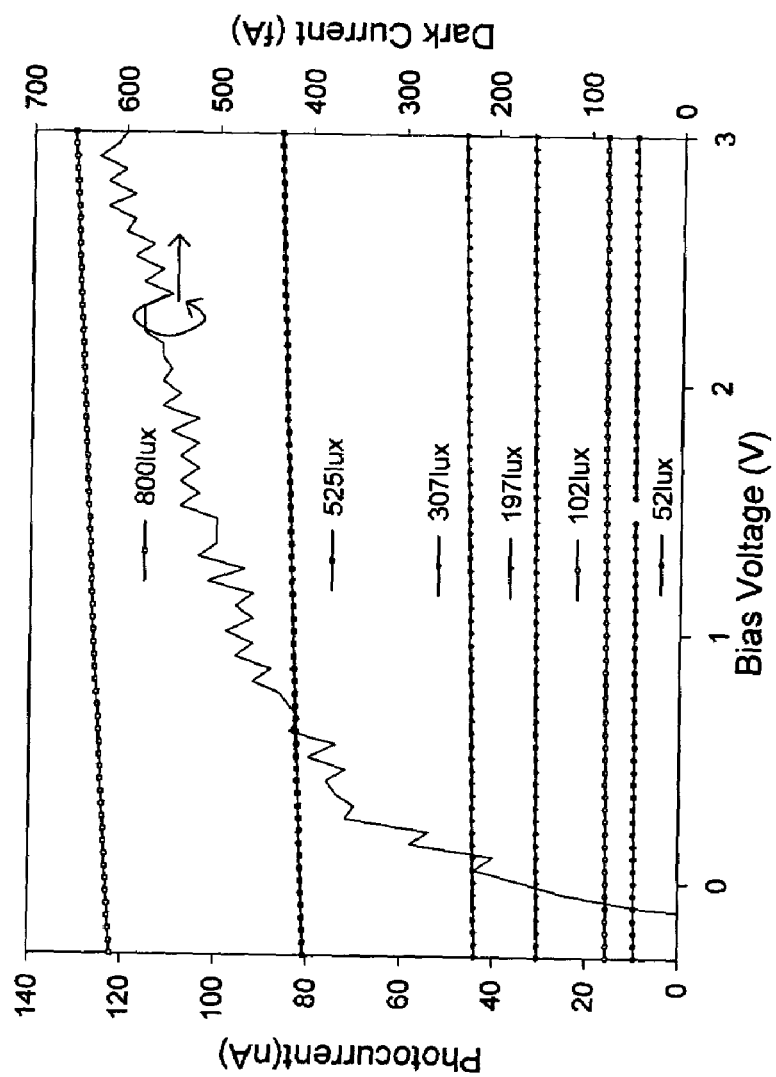
FIG. 12 is a diagram showing experimentally measured photocurrent of a photodiode under different illumination.

Referring to FIG. 11, the DNA chip is exposed in an ordinary tungsten light source of 450 lux. The APS converts the signal from optical domain to voltage domain and the output waveforms from the array for matched and mismatched DNA samples are shown. In addition, referring to FIG. 12, the optical response of the photosensor indicates a sufficiently high dynamic range between the signal and dark current is achieved despite a generic CMOS process used.

Figure 13:
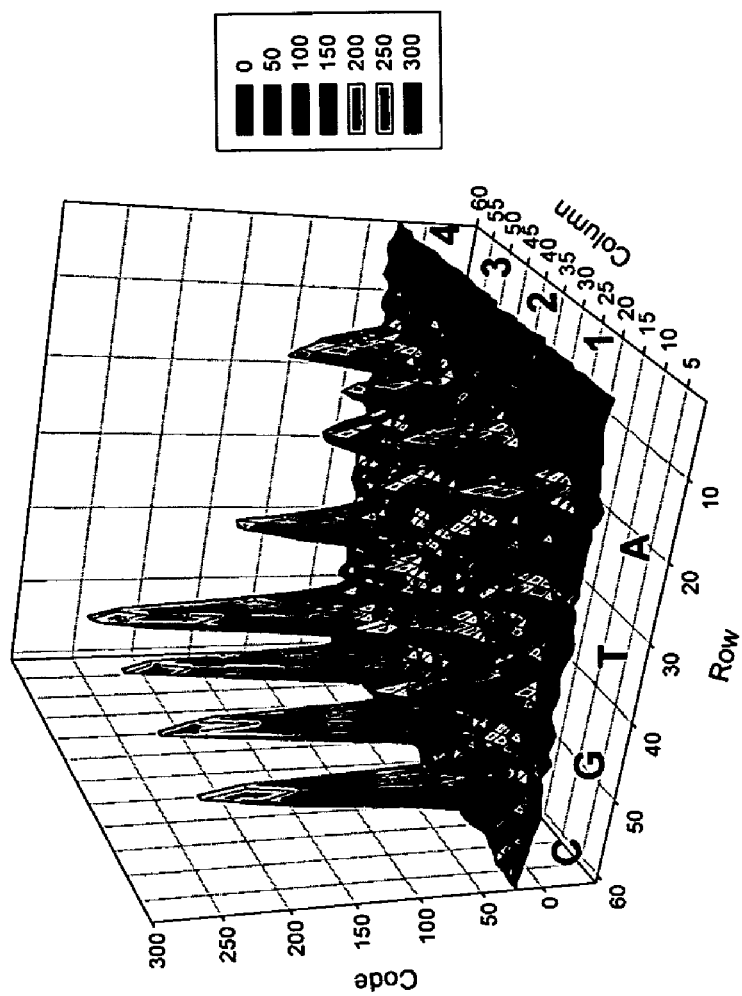
FIG. 13 is a diagram showing experimentally measured captured image and relative intensity for matched and mismatched DNA samples.
Figure 13:
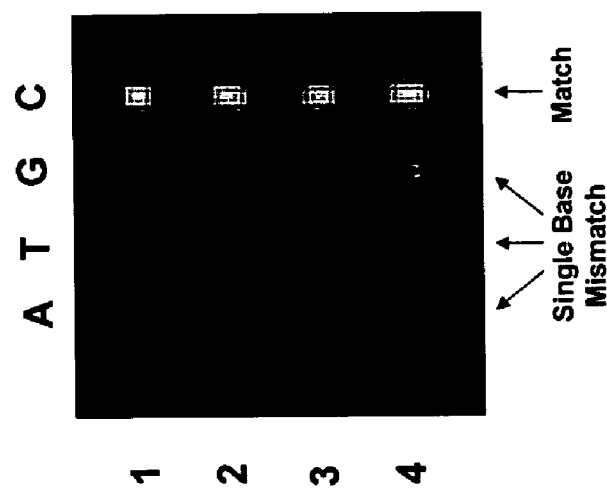

Now referring to FIG. 13, the digital outputs of the DNA chip can be visualized using an 8-bit gray scale image. In particular, an image from the DNA array under common room-light of and its relative intensity are reproduced. The three columns on the left have DNA probes with a single-base mismatched with the samples while DNA probes perfectly matched with samples are located on the right-most column. The matched DNA signal is clearly distinguishable even with a single base mismatch The pictures show that the signal to background ratio has sufficient margins for detection even with an ordinary light source.

Figure 14:
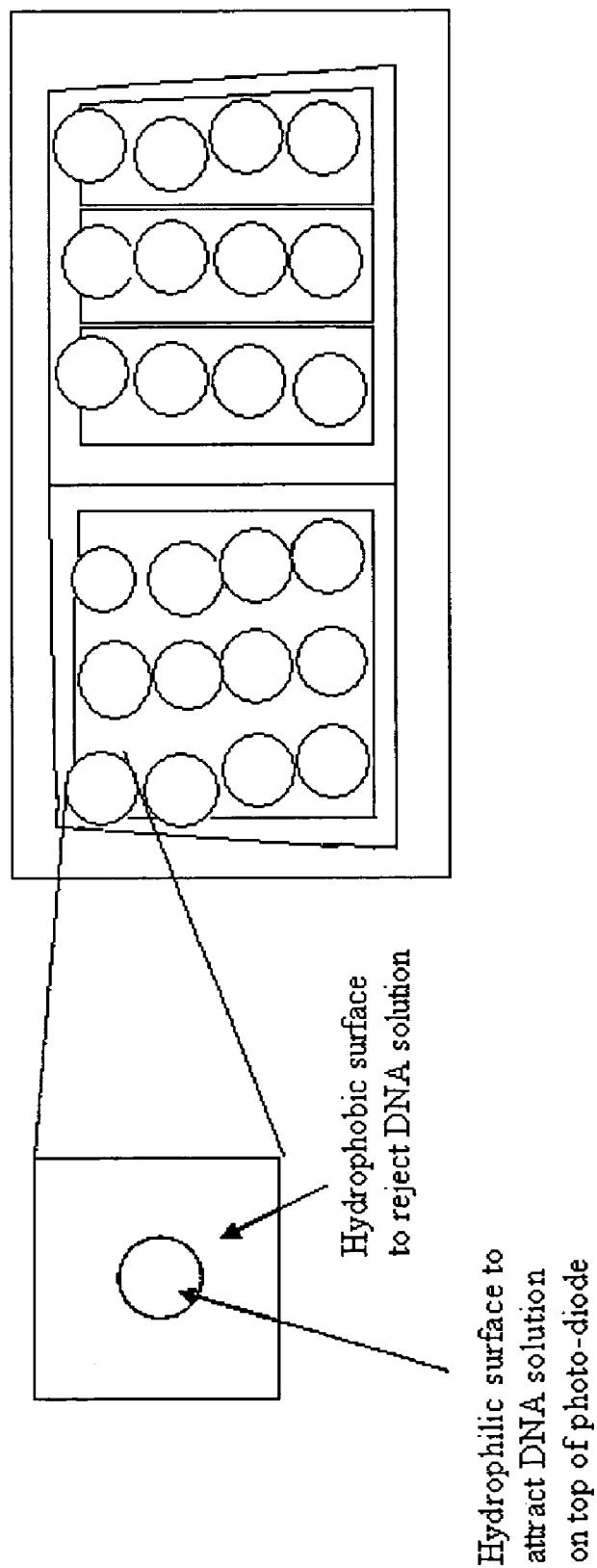
FIG. 14 is a schematic diagram showing how to use different surface property to focus the DNA sample into particular location.

A micro-concentration technique is developed to improve the localization of samples onto the spots with DNA probes and increasing the sensitivity of the micro-array. Referring to FIG. 14, by special surface treatment, the background of the chip outside the detection cell can be making very rough and hydrophobic compared with the region for detection. Such formation of the hydrophilic/hydrophobic region can be realized by chemical means or physical means (such as different surface roughness). In such case, the solution dropped to the chip will be concentrated in the desired area in the form of spherical solution droplet as shown in FIG. 14. After evaporation, DNA samples are "focused" to the site for detection. This technique obviates the need to fabricate "wells" on the surface to contain the DNA probes and samples.

Figure 15:
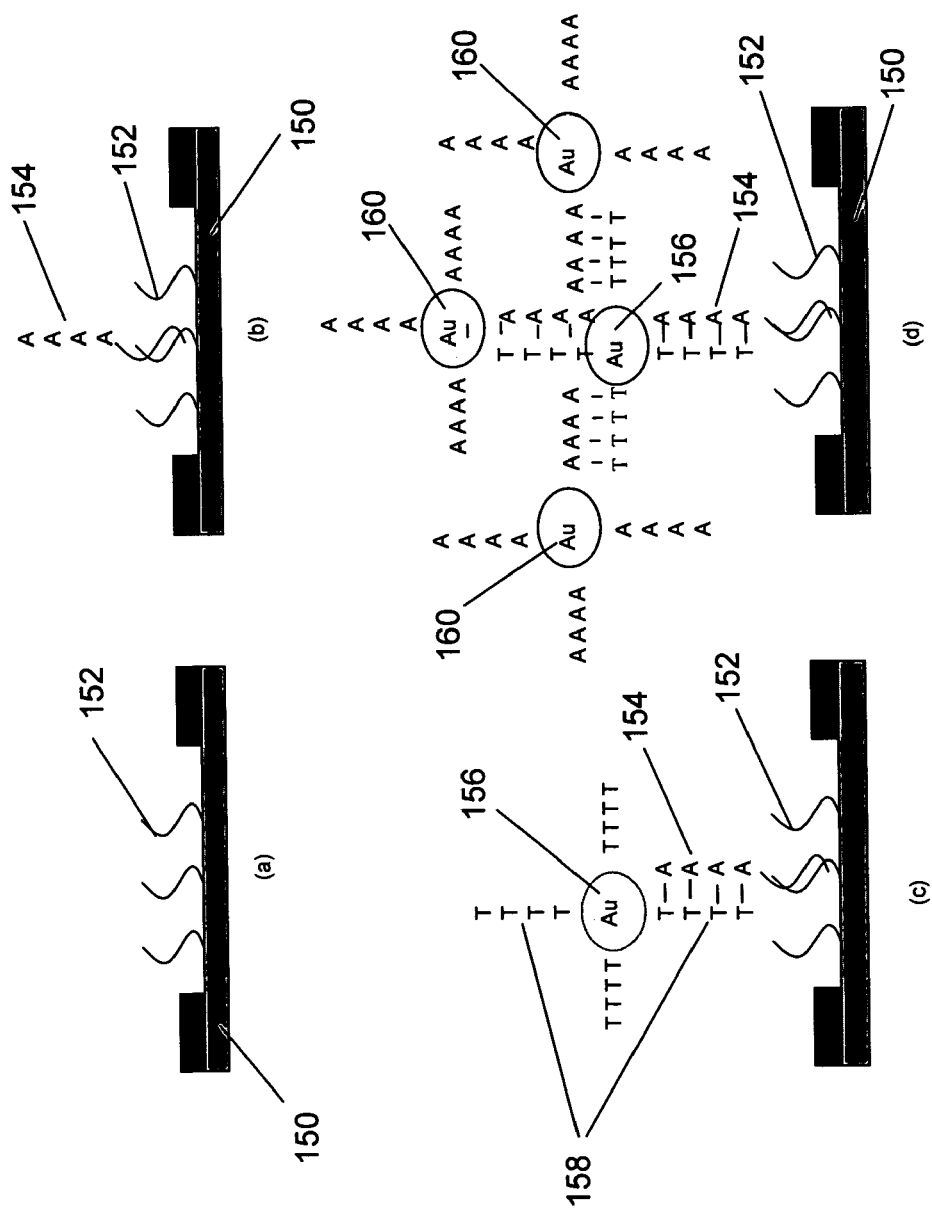
FIG. 15 is a schematic diagram showing a process of multilayer gold particle amplification according to another embodiment of the present invention

In addition, multiple layers of nano-gold particles can be used to increase the thickness of the blocking film and opaqueness, as shown in FIG. 15. For example, silver enhancement to form thicker metal layer as light blockage is shown here. In particular, the process of multi-layer gold particle amplification is shown respectively by FIGS. 15(a) to 15(d):

(a) starting with the DNA array 150 with immobilized DNA probes 152;
(b) adding sample with a polyA tail 154;
(c) adding a first gold particle 156 with multiple polyT DNA strands 158 attached to it and a polyT strands 158 will hybridize with the polyA tail 154 on the attached sample; and
(d) adding second gold particles 160 with polyA DNA strands that would hybridize with the other free polyT DNA strand on the first layer of gold particle 158 forming a second layer of gold particles.

Figure 16:
FIG. 16 is SEM pictures of the DNA detector surface after silver enhancement showing that there is an increasing density of gold nanoparticles.
Figure 16:

The silver enhancement only takes place at locations with gold particle present as the gold particles are needed to act as seeds to initiate the sliver deposition. As shown in FIG. 16, the SEM pictures at the site with matched DNA after 5 mins and 30 mins silver enhancement indicate the successful enlargement of the nano-gold particle.

Figure 17:
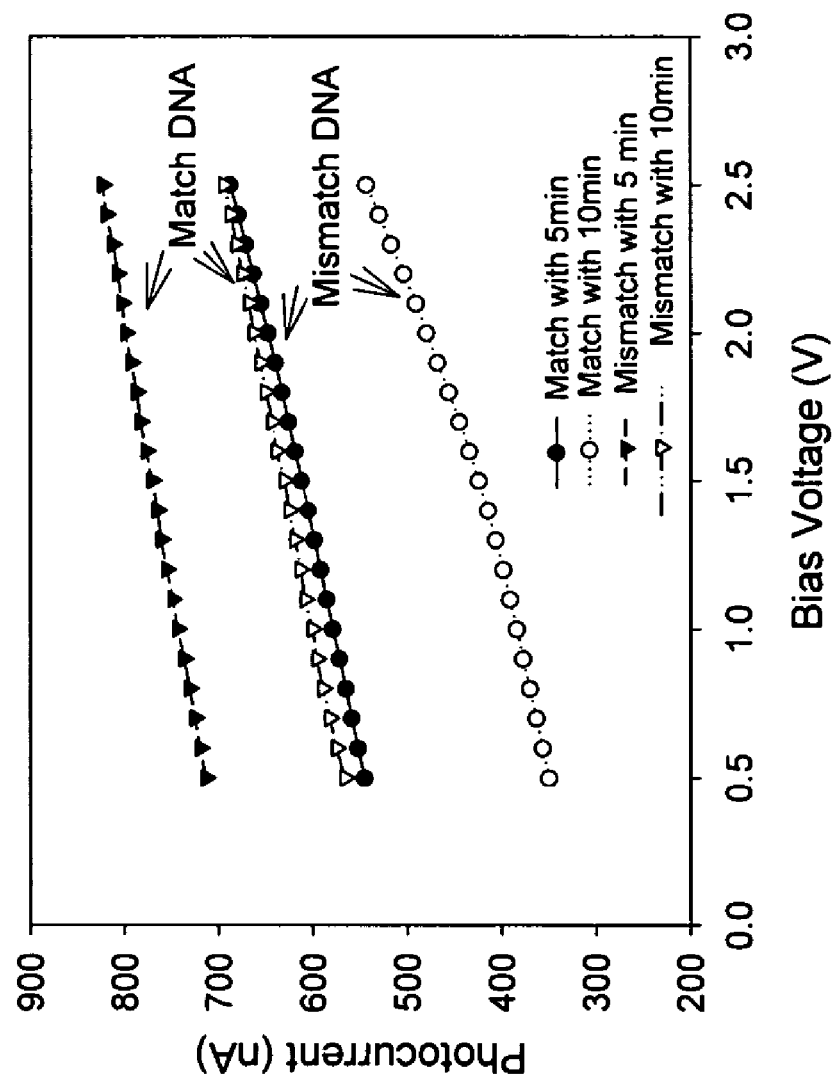
FIG. 17 is a diagram showing experimentally measured photocurrent comparison between match and mismatch DNA samples with two different silver enhancement time.
Figure 18:
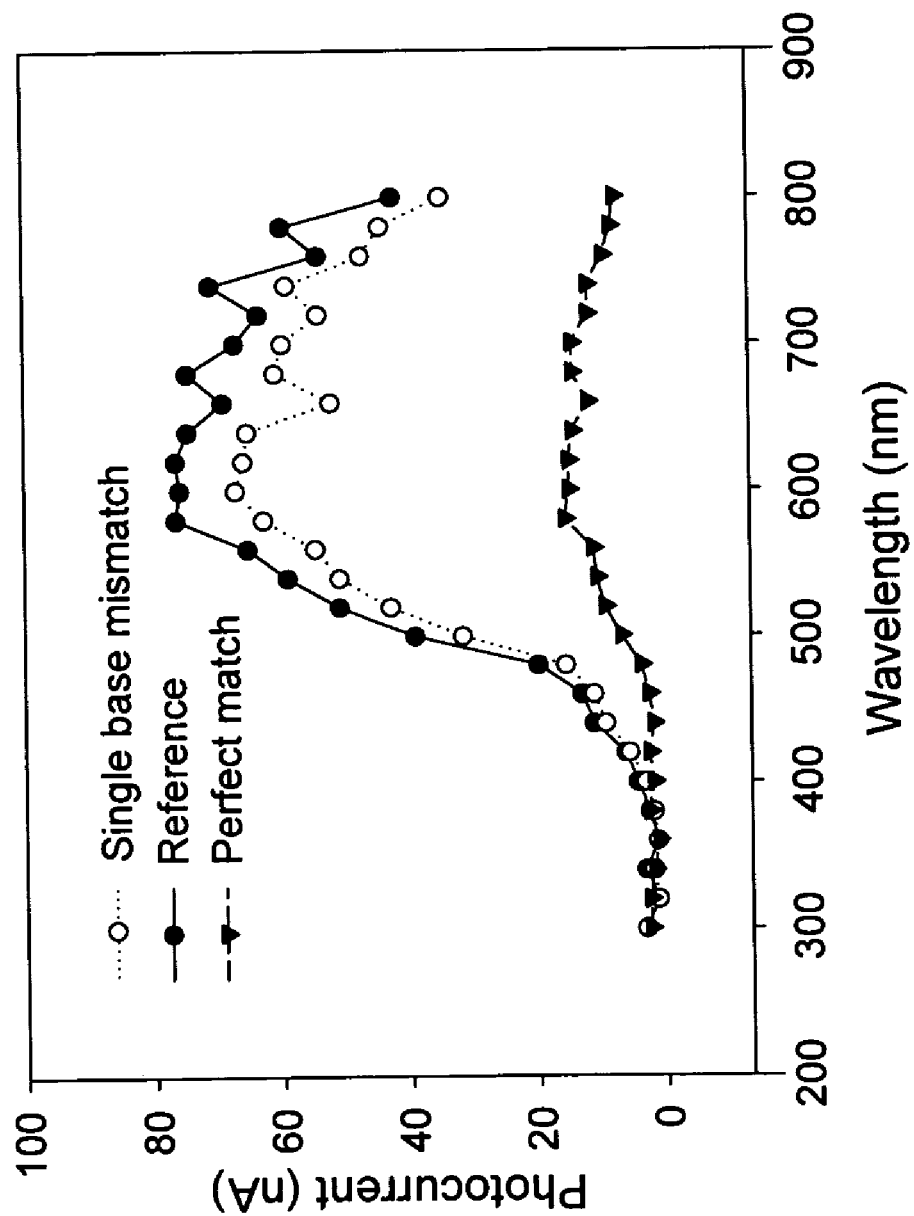
FIG. 18 is a diagram showing experimentally measured spectral response of the detection cell with matched, reference and single base mismatched DNA sample.
Figure 19:
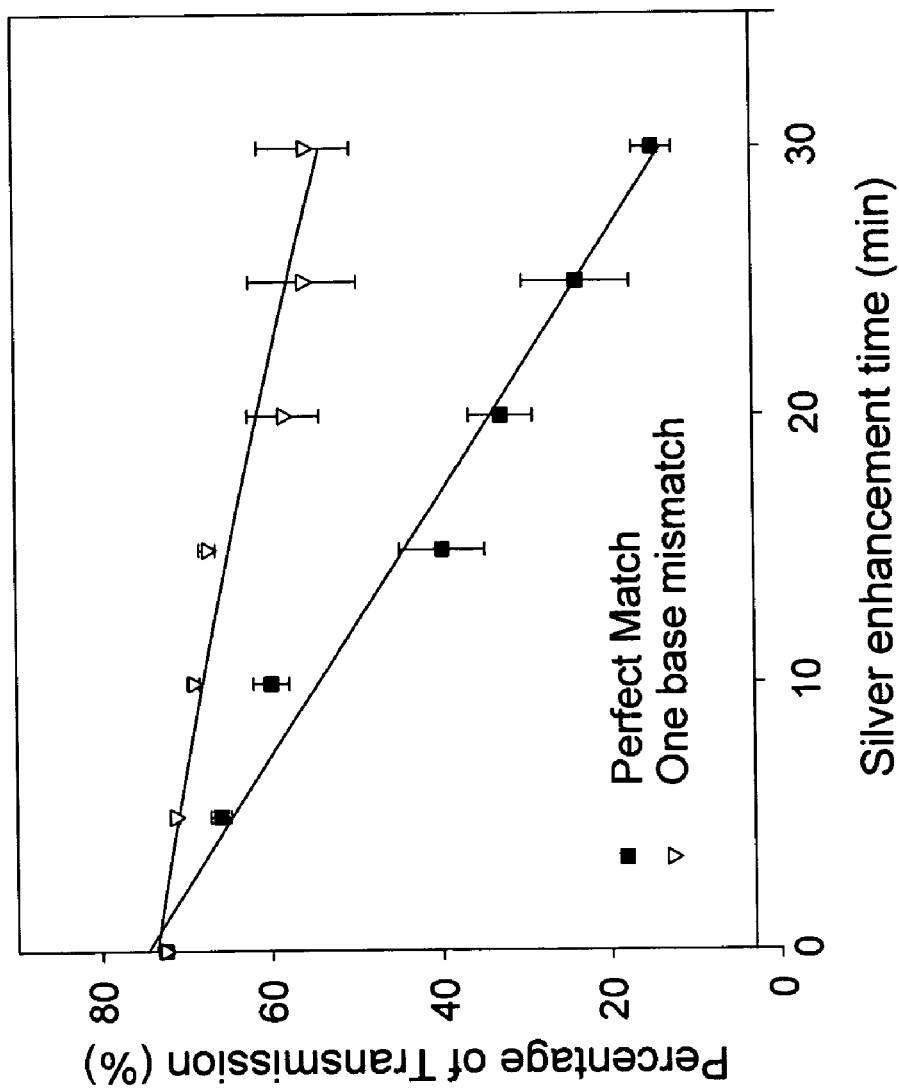
FIG. 19 is a diagram showing experimentally measured transmission property of match and mismatch DNA samples as a function of the silver enhancement time.

FIGS. 17 to 21(b) provide certain experimental results of the IC detector and detection method according to the present invention. In particular, the photodiode current with matched and unmatched samples shows that a significant difference (more than 200%) can be observed between matched and unmatched DNA samples as shown in FIG. 17. In addition, referring to FIG. 18, the spectral response resulting from sensor cells with matched and unmatched DNA under different monochromatic incident light indicates that the system can work with most visible spectrum. Further, the effect of silvers enhancement time on the amount of transmitted light indicates that the silver enhancement time is not critical as shown in FIG. 19.

Figure 20:
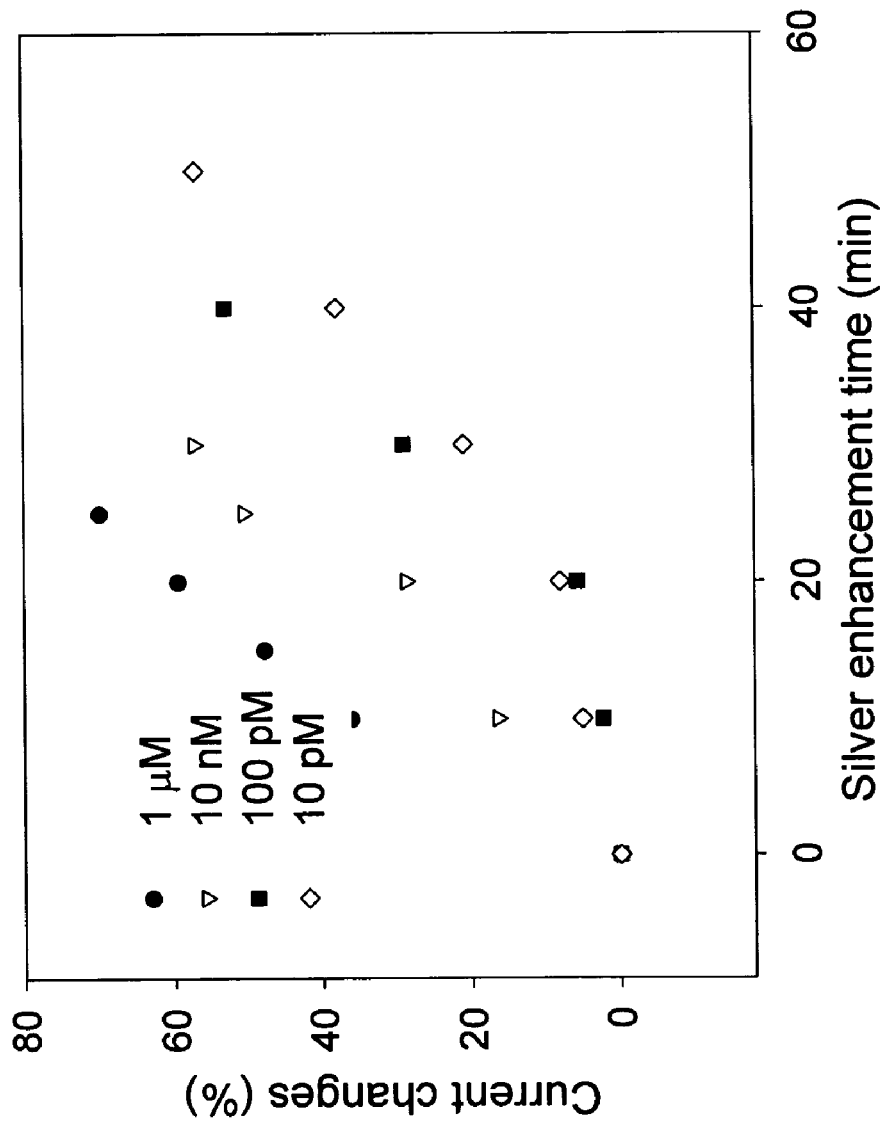
FIG. 20 is a diagram showing experimentally measured current change illustrating relationship between electrical currents and target DNA concentrations.

In FIG. 20, by increasing the silver enhancement time, the sensitivity of the optical detection can be increased, and it has been demonstrated that an extremely low DNA concentration down to 10 pM can be detected. This sensitivity has significantly surpassed that of existing fluorescence based detection method of prior art.

Figure 21A:
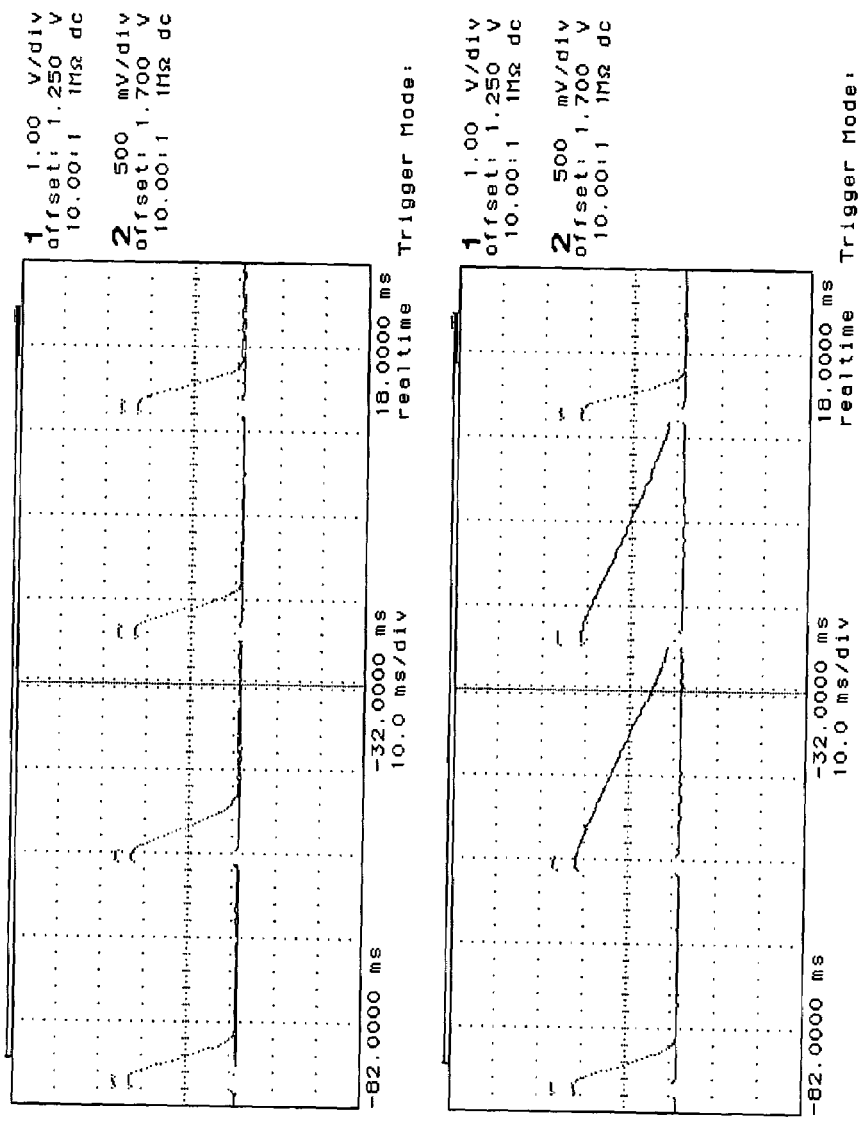
FIG. 21(a) is a diagram showing experimentally measured output voltage waveform from underneath active pixel sensor (one DNA probe covers two detection cells) with halogen 80 W light source.
Figure 21B:
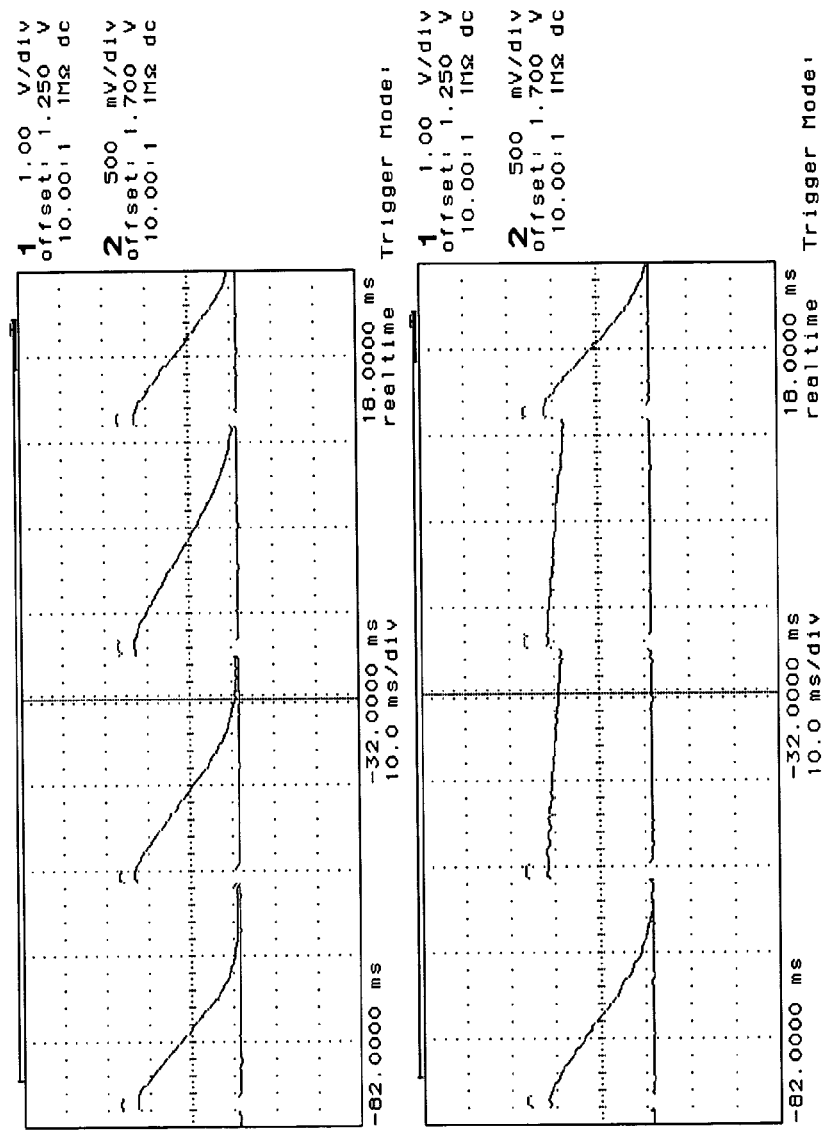
FIG. 21(b) is a diagram showing experimentally measured output voltage waveform from underneath active pixel sensor (one DNA probe covers two detection cells) with common room light source of 450 lux.

Finally, referring to FIG. 21(a) and FIG. 21(b), the voltage outputs from the APS are shown for the match and mismatch DNA samples. In particular, FIG. 21(a) shows output voltage waveform from underneath active pixel sensor (one DNA probe covers two detection cells) with halogen 80 W light source, and FIG. 21(b) shows output voltage waveform from underneath active pixel sensor (one DNA probe covers two detection cells) with common room light source of 450 lux. Experimental results show that the system can be used with a wide range of light sources unlike existing detection systems that rely on UV light sources for fluorescence excitation It should be noted that even a single base mismatch can be detected with our system.

The present invention has been described in detail herein in accordance with certain preferred embodiments thereof. To filly and clearly describe the details of the invention, certain descriptive names were given to the various components. It should be understood by those skilled in the art that these descriptive terms were given as a way of easily identifying the components in the description, and do not necessarily limit the invention to the particular description. For example, the substrates are typically made from SiO2, but may be made of any material that can have a surface treatment for coating of test sample. Also, while gold particles are typically used, any nano-opaque particles may also be applied to the test sample.

While the sample is typically a DNA fragment, it may be anything or any biological samples. Extending from the example taught above, a person skilled in the art will appreciate that, instead of immobilizing DNA probes 84 on the photodiode surface 82 of the chip, it is equally feasible to immobilize the sample fragments onto the surface instead. In this second embodiment modified from the first embodiment described above, probes with Poly A tails may then be applied in the first hybridization step and any unbound probes washed off. Thereafter, the bound probes with the Poly A tails may be visualized by the application of nano-gold particles followed by enhancement with silver as taught above.

A third embodiment of the present invention is one where known ribonucleic acid (RNA) may be used as probes to bind to unknown RNA (that is, RNA-RNA hybridization) or to DNA (for example, in DNA-mRNA hybridization) to identify and detect the presence of sequences in the sample that are complementary to those of the probes.

A fourth embodiment of the present invention is for protein-protein binding such as for enzymes and enzyme substrates. Under certain conditions, the complex formed by an enzyme with its enzyme substrate may be irreversible and thus the structure of the complex may be maintained and visualized. An advantage of his embodiment wherein enzymes are used is that the bound protein may be modified to have another enzymatic site that is involved in a change of the opaqueness of the light transmitted through conversion of a clear reactant to a visible or colored reactant In such an embodiment, the use of nano particles may be obviated.

Besides protein-protein binding, the present invention may be readily adapted by a person skilled in the art in a fifth embodiment that utilizes antibody-antigen binding. This is differentiated from the above protein-protein binding as not all antigens are proteins while all antibodies are proteins. The antibody-antigen complex may be naturally irreversible, unlike that of enzyme and enzyme substrate binding.

It is readily apparent from the above examples that numerous types of biological detection principles may be adapted for use in the present invention. For example, the principles employed in enzyme-linked immunosorbent assay (ELISA), radioimmunoassay (RIA) and DNA microarray detection by radioactivity or fluorescence, etc, may be modified for use in the present invention. The primary difference is that the delicate or costly illumination and detection systems required in those techniques have been rendered unnecessary—and indeed obsolete—by the present invention.

The sixth embodiment of the present invention is in a related field. A person skilled in the chemical arts will appreciate that the present invention may be used for chemical reactions in which a first surface-bound compound or molecule reacts with another compound or molecule that is applied to form a complex or precipitate. The mass or quantity complex or precipitate that is formed will affect the transmission of light through the photodiode surface to the sensor array and may thus be measured.

Thus, the present invention may be used for the detection of minute amounts of chemicals in the environment such as pollutants or chemical weapons. The ability of the invention to be highly portable and its independence of a dedicated light source render it eminently suitable for such applications under rugged field conditions.

It will be clear to a person skilled in the art, that, from the many examples above, any type of biological or chemical reaction taking place on the surface of the photodiode surface that changes the quantity of light directed on the surface such that a signal may be detected by the underlying sensor array, is within the scope of the present invention.

Further, certain size of the IC detector is provided, but the present invention is not limited to the provided certain size of the IC detector. The IC detector according to the present invention can be made of any size if necessary.

Therefore, many such modifications are possible. Accordingly, it is intended by the appended claims to cover all such modifications and changes as falling within the true spirit and scope of the present invention.

What is claim is:

1. An integrated circuit (IC) optical detector comprising:
    a substrate, said substrate having a plurality of test sites defined thereon; said test sites including a surface suitably treated for binding with at least one test sample;
        said at least one test sample having a sequence complementary to one or more modified metal particles; and
        an IC, said IC incorporating at least one optical sensor array for simultaneously receiving and sensing optical signals from said test sites during operation; wherein
    presence of said at least one test sample attached with said one or more modified metal particles at a test site changes the quantity of light directed through the test site; the change in quantity of light being optically detectable by said optical sensor array; said optical sensor array further converting sensed optical signals to electrical signals; and said IC automatically processing and outputting said electrical signals during operation.

2. The detector of claim 1, wherein said substrate has physical surface treatment to create said test sites.

3. The detector of claim 1, wherein said substrate has chemical surface treatment to create said test sites.

4. The detector of claim 1, wherein said substrate has surface treatment to coat at least one biological molecule to create said test sites.

5. The detector of claim 4, wherein the biological molecule is deoxyribonucleic acid (DNA).

6. The detector of claim 4, wherein the biological molecule is ribonucleic acid (RNA).

7. The detector of claim 4, wherein the biological molecule is a protein molecule.

8. The detector of claim 1, wherein said IC is capable of identifying a location of said test sample.

9. The detector of claim 1, wherein said at least one optical sensor array is a photodiode array.

10. The detector of claim 1, wherein said at least one optical sensor array is a CMOS image sensor array.

11. The detector of claim 1, wherein said at least one optical sensor array is a CCD array.

12. The detector of claim 1, wherein said test sample is a DNA fragment.

13. The detector of claim 1, wherein said substrate additionally comprising an external surface surrounding said plurality of test sites which is rough and hydrophobic compared with said plurality of test sites.

14. The detector of claim 1, wherein presence of said at least one test sample attached with said one or more modified metal particles at a test site changes the quantity of visible light directed through the test site; the change in quantity of visible light being optically detectable by said optical sensor array.

* * * * *

UNITED STATES PATENT AND TRADEMARK OFFICE
CERTIFICATE OF CORRECTION

PATENT NO. : 7,585,664 B2  Page 1 of 1
APPLICATION NO. : 10/965270
DATED : September 8, 2009
INVENTOR(S) : Chan et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 870 days.

Signed and Sealed this

Fourteenth Day of September, 2010

David J. Kappos
*Director of the United States Patent and Trademark Office*